United States Patent
Gip et al.

(10) Patent No.: US 7,330,250 B2
(45) Date of Patent: Feb. 12, 2008

(54) NONDESTRUCTIVE EVALUATION OF SUBSURFACE DAMAGE IN OPTICAL ELEMENTS

(75) Inventors: Tung Say Gip, San Jose, CA (US); Reinhold Garbe, San Jose, CA (US); Quoc Nguyen, San Jose, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 270 days.

(21) Appl. No.: 10/848,890

(22) Filed: May 18, 2004

(65) Prior Publication Data

US 2005/0259248 A1    Nov. 24, 2005

(51) Int. Cl.
*G01N 21/88* (2006.01)

(52) U.S. Cl. ............... 356/239.2; 356/237.2

(58) Field of Classification Search .. 356/239.1–239.8, 356/237.1, 349, 429–430; 451/34, 36–37; 382/141; 250/234, 201.3, 226
See application file for complete search history.

(56) References Cited

U.S. PATENT DOCUMENTS

| | | | |
|---|---|---|---|
| 4,411,525 A | | 10/1983 | Ogawa |
| 4,957,670 A | * | 9/1990 | Myers et al. ............... 264/40.1 |
| 5,155,553 A | * | 10/1992 | Chen .......................... 356/457 |
| 5,343,038 A | * | 8/1994 | Nishiwaki et al. .......... 250/234 |
| 5,369,488 A | * | 11/1994 | Morokuma ................ 356/493 |
| 5,424,536 A | * | 6/1995 | Moriya ...................... 250/225 |
| 5,477,732 A | * | 12/1995 | Yasue et al. ................. 73/105 |
| 5,726,748 A | * | 3/1998 | Morris ..................... 356/237.2 |
| 5,781,294 A | * | 7/1998 | Nakata et al. ............... 356/487 |
| 5,894,345 A | * | 4/1999 | Takamoto et al. ........ 356/237.1 |
| 5,936,726 A | * | 8/1999 | Takeda et al. ............ 356/237.2 |
| 5,953,130 A | * | 9/1999 | Benedict et al. ............ 356/429 |
| 6,099,389 A | * | 8/2000 | Nichols et al. ................ 451/36 |
| 6,285,449 B1 | * | 9/2001 | Ellingson et al. ......... 356/237.1 |
| 6,476,909 B1 | * | 11/2002 | Nakayama et al. ....... 356/239.2 |
| 6,661,523 B1 | * | 12/2003 | Rubinstein et al. ......... 356/601 |
| 6,766,046 B1 | * | 7/2004 | Saito et al. .................. 382/141 |
| 7,042,556 B1 | * | 5/2006 | Sun .......................... 356/4.07 |

FOREIGN PATENT DOCUMENTS

| | | |
|---|---|---|
| EP | 0 319 797 | 11/1988 |
| JP | 06 109646 | 4/1994 |
| JP | 2001091470 A * | 4/2001 |

OTHER PUBLICATIONS

Lasertec, Blue Laser Microscope VL2000 brochure (Aug. 2000) pp. 1-4.
Brown, Norman J., "Lapping: Polishing and Shear Mode Grinding" pp. 1-12, (May 23, 1991).

(Continued)

*Primary Examiner*—Sang H. Nguyen

(57) ABSTRACT

A non-destructive process for evaluating subsurface damage in an optical element focuses a microscope at points within the optical element and measures the intensity of reflected light. In one embodiment, a microscope focus a laser beam at a measurement point with the optical element and also collects reflected or scattered light from damage in the optical element. Analysis of data indicating the reflected intensities for a three-dimensional array of points within the optical element can determine the location and severity of the subsurface damage.

12 Claims, 3 Drawing Sheets

OTHER PUBLICATIONS

Brown, Norman, "Memo on Fracture and Fractureless Grinding" (May 23, 1991) pp. 1-7.

Brown, Norman J. et al., "Optical Polishing of Metals" SPIE vol. 306 Contemporary Methods of Optical Fabrication (1981) pp. 42-55.

Brown, N.J., "Some speculations on the mechanisms of abrasive grinding and polishing" Precision Engineering (Jul. 1987) vol. 9, No. 3, pp. 129-137.

Carr, Jeffrey W. et al., "Subsurface Structure in Polished Fused Silica and Diamond Turned Single Crystal Silicon" (Jun. 1999) Lawrence Livermore National Laboratory UCRL-JC-134512 Preprint.

Roberts, S.G. et al., "Final Report: Quantitative NDT of Surface Damage in Glass and Ceramics" Dept. of Materials, Oxford University, GR/L/27633, pp. 1-6, May 2003.

Roberts, S.G. et al., Final Report: Characterisation of Surface Roughness and Sub-surface Damage Dept. of Materials, Oxford University, GR/J08485 (May 28, 2003) pp. 1-9 http://users.ox.ac.uk/~roberts/sgrgroup/grants/J08485.htm.

"Subsurface Damage in Microgrinding Optical Glasses" LLE Review, (Oct.-Dec. 1997) vol. 73, pp. 45-49, May 2003.

* cited by examiner

NONDESTRUCTIVE EVALUATION OF SUBSURFACE DAMAGE IN OPTICAL ELEMENTS

BACKGROUND

Optical elements often contain subsurface damage such as cracks, voids, or contaminant particles. This subsurface damage may be inherent to the type or quality of the material used in the optical element or may be produced during fabrication processes such as sawing, grinding, and polishing. Regardless of the source, the amount of subsurface damage in precision optical elements often needs to be evaluated because the subsurface damage can affect the performance of the optical element. In particular, subsurface damage in an optical path of an optical element can cause light absorption and scattering that may lead to heat generation or a poor quality optical signal.

Non-destructive techniques that measure the surface profile of optical elements are known but generally do not provide sufficient information about the subsurface damage.

One technique for evaluating the subsurface damage in an optical element is to mathematically model the optical element based on knowledge of the materials and fabrication processes employed. With an accurate model, the expected damage in a particular design can be determined. However, such models will be inaccurate if the model is based on inaccurate characterizations of the material or the fabrication process or if effects not anticipated in the model cause damage. Further, even when a model is accurate, the level of subsurface damage in individual optical elements is generally subject to variations, and a specific optical element may have more or less subsurface damage than expected.

A number of destructive evaluation techniques are available for measurement of subsurface damage. A taper grinding process, for example, can cut into samples of an optical element design to expose the subsurface damage for evaluation. Alternatively, damage at an optical surface can be enlarged or exposed using an acid etch. The acid etch generally has greater effects on cracks, thereby permitting surface examination with a high power microscope to detect the enlarged or exposed cracks or defects. These destructive techniques avoid the need to accurately model materials or the fabrication processes used in an optical design. However, each optical element evaluated in this manner is generally destroyed or rendered unusable, which is very undesirable for expensive systems or elements. Also, destructive evaluations only measure typical subsurface damage for a design. The problem of variations in optical elements that are not directly evaluated leaves uncertainty in the amount of subsurface damage in the useable optical elements. Further, the results of a destructive evaluation can typically take several days to obtain.

Acoustic measuring techniques, for example, combining Hertzian Acoustic Emission Indentation (HAEI) and a Line Focus Acoustic Microscope (LFAM), can examine the surface condition and fracture toughness of an optical element. However, such techniques have difficulties in detecting defects larger than about 10 µm and also require expensive equipment that requires a significant amount of skill, training, and support to operate.

Efficient techniques for non-destructive evaluation of subsurface damage in optical elements are accordingly sought.

SUMMARY

In accordance with an aspect of the invention, equipment such as a laser microscope conventionally used for surface plotting can non-destructively evaluate subsurface damage in an optical element. In one embodiment of the invention, a measurement device that normally uses light that reflects from the air-surface interface of an optical element to locate surface elevations is operated to focus at a range of points that extend into the optical element being tested. An increase or peak in the reflected light measured for a focus point within the optical element indicates scattering or reflection from a defect or damage within the component. The area over which defects extend and the intensity of the light provide indications of the severity of the subsurface damage. Conversion factors, tables, or functional relations between the measured intensity of scattered light and the characteristics of subsurface defects can be developed for specific measurement equipment and measured materials.

One specific embodiment of the invention is a process for evaluating subsurface damage in an optical element. The process includes illuminating the optical element; focusing a measurement device such as a microscope at a measurement point that is within the optical device and measuring an intensity of scattered light collected by the measurement device when focused at the current point. The measurement point can be changed (e.g., by scanning across the surface of the optical element, and the measurement of scattered light from within the optical element can be repeated.

Another specific embodiment of a process for evaluating subsurface damage in an optical element, includes: scanning a focus of a laser microscope down to a target depth within the optical element; measuring an intensity of scattered light collected while scanning the focus into the optical element; and determining a location of a subsurface damage in the optical element from the intensity of the scattered light.

BRIEF DESCRIPTION OF THE DRAWINGS

Use of the same reference symbols in different figures indicates similar or identical items.

DETAILED DESCRIPTION

In accordance with an embodiment of the invention, a measurement system such as a laser microscope suitable for scanning of an optical surface is used to scan the interior of an optical element. While scanning into the optical element, the intensity of light reflected or scattered in the optical element is measured, and analysis of the measured intensity data provides an indication of subsurface damage in the optical element.

Figure 1:
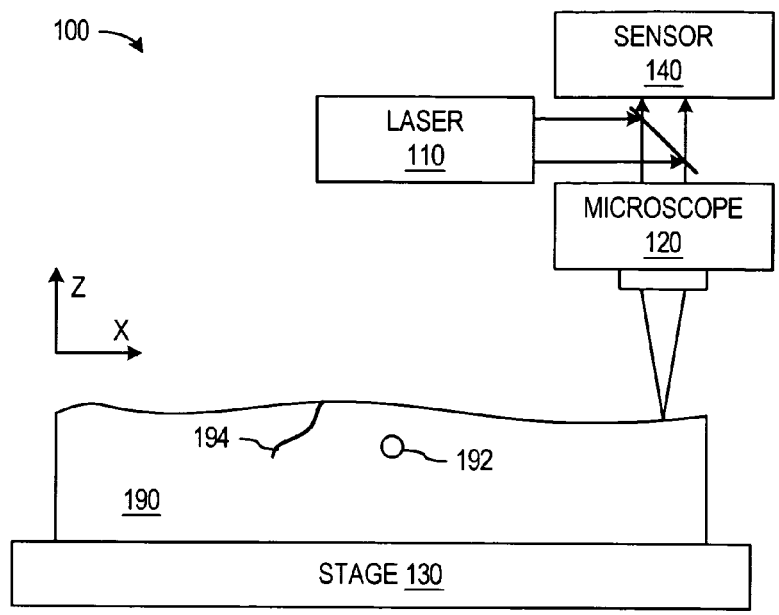
FIG. 1 shows a laser microscope suitable for measurement subsurface damage.

FIG. 1 schematically shows a laser microscope 100 in a conventional configuration for measuring the elevation of a point on a surface of an optical element 190. Laser microscope 100 includes a laser 110, a microscope 120, a sensor 130, and a precision stage 140. Microscope 120 focuses a beam from laser 110 at one of its a focal points, and sensor 130 measures the reflected light that microscope 120 collects. In one particular embodiment of the invention, laser microscope 100 can be a VL200 Blue Laser Microscope, which is commercially available from Lasertec Corporation of Yokohama, Japan. However, for evaluation of subsurface damage (e.g., cracks, voids, and contaminant particles) having a typical dimension of about 2 to 3 microns or larger for an unpolished surface, a laser with a longer wavelength laser (e.g., a red laser diode) may be better for detection of the subsurface damage.

A conventional operation of laser microscope 100 can measure the elevation of a point on the surface of a device such as optical element 190. To measure surface elevation, a point on optical element 190 is positioned under microscope 120, and stage 140 moves optical element 190 in a z direction (i.e., to control the separation between microscope 120 and optical element 190) as required to maximize the intensity that sensor 130 measures. The maximum intensity corresponds to the configuration illustrated in FIG. 1A, where the focal point of microscope 120 is at the surface of optical element 190. The z coordinate setting of stage 140 (and x and y settings) when sensor 130 measures the maximum intensity can be read out to indicate the elevation (and location) of the point on the surface of optical element 190. Stage 140 can then scan optical element 190 in a horizontal direction (e.g., the x direction) while repeating the focusing operation for measurement of the elevations at a series of points on optical element 190. A laser microscope as conventionally used can thus measure the surface profile or surface roughness of optical element 190.

Figure 2:
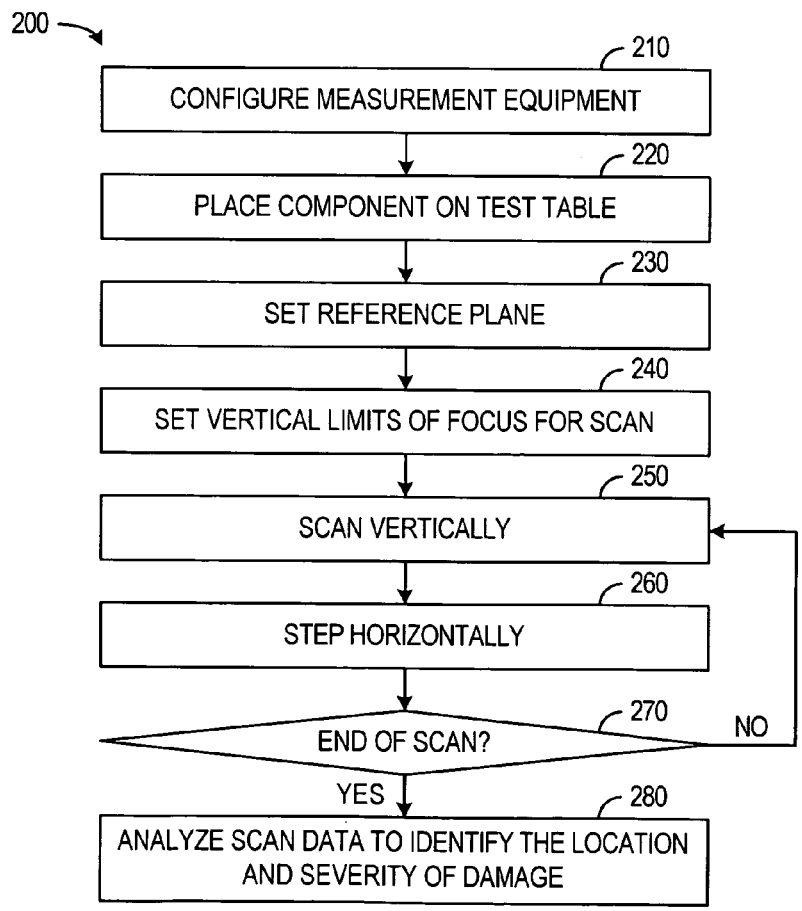
FIG. 2 is a flow diagram of a process in accordance with an embodiment of the invention for non-destructive measurement of subsurface damage in an optical element.

FIG. 2 illustrates a flow diagram for a process 200 that scans an optical element to detect subsurface damage or defects. Process 200 can generally be used to evaluate an optical element that is a separate device or that is an integrated portion of a system such as an electro-optical component. In an exemplary embodiment, process 200 uses a laser microscope of the type described above, but any other type measurement device capable of measuring reflected light for a range of depths within an optical element could be used. For illustrative purposes, the following describes the example of using the laser microscope 100 of FIGS. 1, 3, 4, and 5 in an evaluation of subsurface damage.

Process 200 begins in a step 210 by configuring the measurement equipment (e.g., laser microscope 100) for subsurface measurement. Such configuration may include selection of an optical wavelength for a laser source 110, a number of horizontal scan lines, the length of each scan line, and the separation between the scan lines. Configuration step 210 can thus select the area of optical element 190 that will be scanned.

The component being tested (e.g., optical element 190) is mounted in the measurement equipment in step 220. In particular, the component can be place on a test table or precision stage that permits controlled movement of the component (e.g., relative to the microscope 120). Movement of the component can thus select a measurement point. Alternatively, moving the measurement equipment (e.g., moving microscope 120) or moving a scan beam could alternatively control the location of a measurement.

Step 230 establishes or sets a reference plane that is preferably near the surface of the component being evaluated, and step 240 sets vertical scan limits relative to the reference plane. The scan limits are preferably selected so that an upper limit is at least as high as the surface of the component being evaluated and the lower limit extends into the component to at least a desired depth for subsurface damage evaluation.

Figure 3:
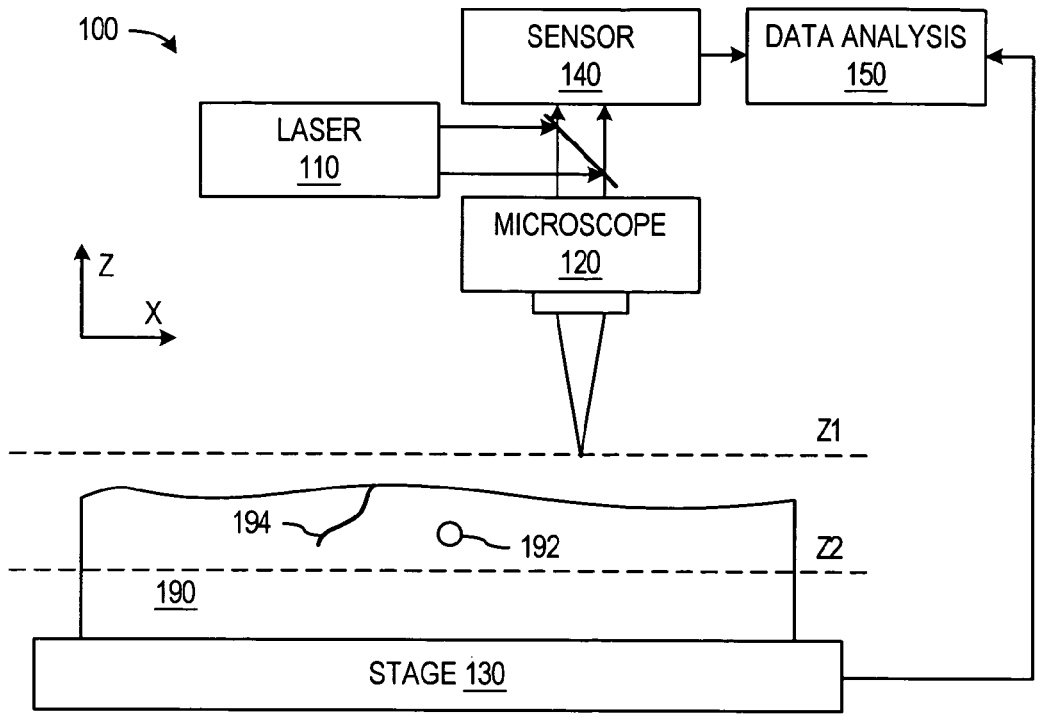
FIGS. 3, 4, and 5 show different configurations of a laser microscope during a subsurface measurement process in accordance with an embodiment of the invention.

FIG. 3 illustrates the location of an upper limit Z1 and a lower limit Z2 for a vertical scan of optical element 190. The desired depth of the scan into optical element 190 will generally depend on the type of optical element 190 being tested. However, as an example, a depth of about 1 to 100 μm may be typical for a precision optical element made of an optical quality glass such as BK-7 where the subsurface damage being evaluated is due to machining such as grinding, diamond turning, polishing, or other material removal methods.

Figure 4:
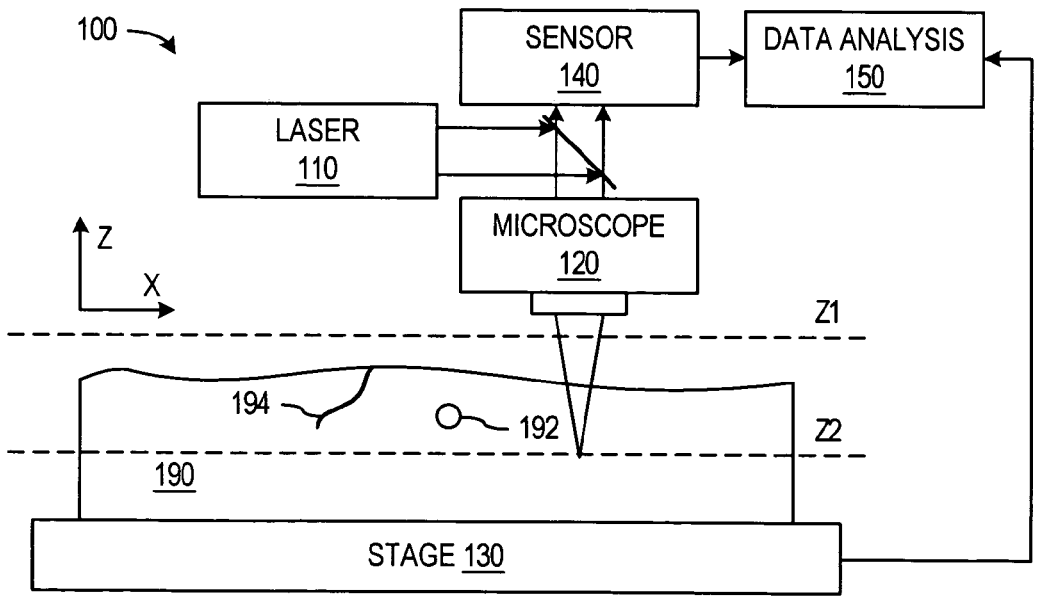

Step 270 scans optical element 190 vertically relative to microscope 120 so that the focal point of microscope 120 moves between the upper limit Z1 and the lower limit Z2. FIGS. 3 and 4 respectively illustrate configurations where the focus of microscope 120 is at the upper and lower limits Z1 and Z2 of a vertical scan. During movement from the configuration of FIG. 3 to the configuration of FIG. 4, sensor 140 measures the intensity of light reflected back into microscope 120, and the intensity measurements for a series of vertical positions of the focal point of microscope 120 can be recorded in an analysis system 150. The intensity measurements generally increase as the focal point of microscope 120 approaches the surface of optical element 190 but fall as the focal point moves away from the surface. If optical element 190 is damage free along the range of the vertical scan, intensity measurements will only have one peak, and that peak corresponds to the focus of microscope 120 being at the surface of optical element 190.

Step 260 horizontally moves optical element 190 relative to the rest of the system to thereby change the measurement point. If decision step 270 determines that scanning is not yet complete, process 200 branches from step 270 back to step 250 and vertically scans into optical element 190.

Figure 5:
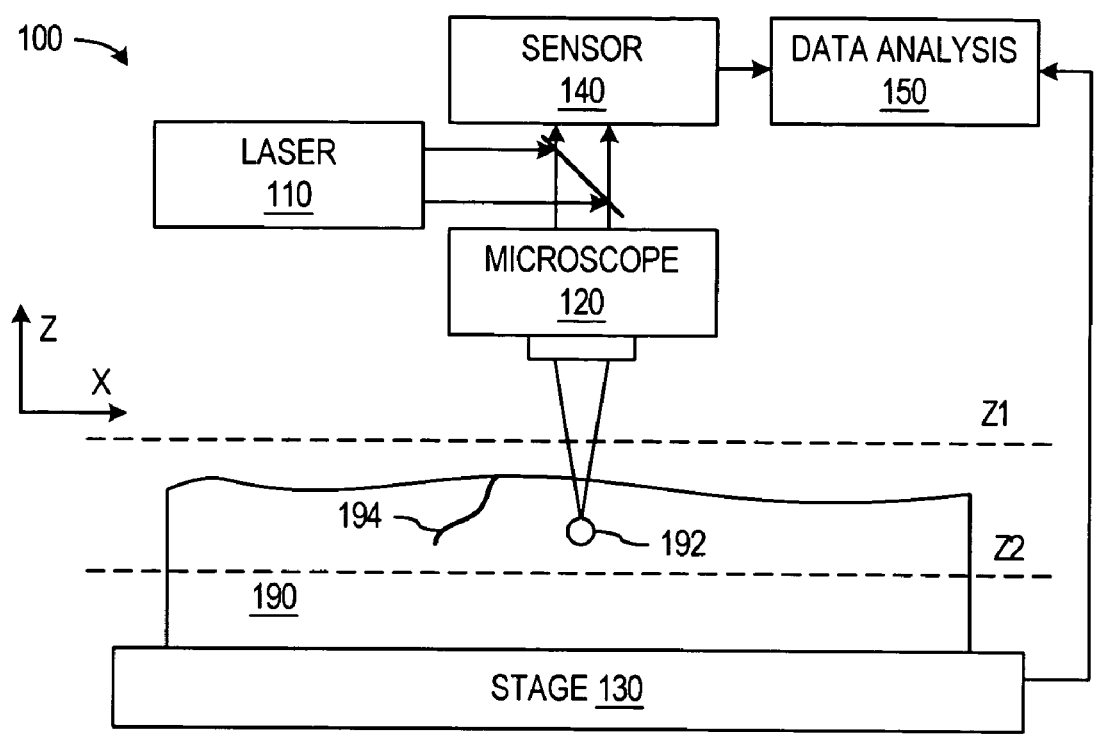

FIG. 5 illustrates a configuration of laser microscope 100 when a horizontal movement in step 270 positioned microscope 120 over a defect 192 in optical element 190 and vertical scanning in step 260 brought the focus of microscope 120 to defect 192. Sensor 130 detects defect 192 as an increase in the reflected light that microscope 120 collects when the focal point nears defect 192 and/or a drop in measured intensity as the focal point moves past defect 192. Accordingly, a vertical scan corresponding to the horizontal position shown in FIG. 5 records intensity data having a first peak when the focal point is at the surface of the optical element 190 and a second peak when the focal point is at defect 192. The magnitude of an intensity peak may depend on the type of material in optical element 190, the severity of the defect 192, and the depth of the defect 192. The same defect 192 may be found in multiple repetitions of vertical scan step 250, and the number of vertical scans detecting damage indicates the dimension or area of the defect 192. A crack 194, for example, may extend over a relatively large area of optical element 190.

When decision step 270 determines that the scan is complete, process 200 of FIG. 2 branches from step 270 to step 280 and analyzes the recorded intensity data to evaluate the subsurface damage within the scanned area of the component. As mentioned above, the analysis can identify the extent or location of damage by identifying the locations for vertical scans that detect damage and can determine the severity of the damage from the measured intensities at different depths.

In one embodiment, the data for analysis includes a three-dimensional array of intensity measurements, which are indexed by the vertical and horizontal coordinates of the measurement points. Data analysis system 190, which can be implemented in software or firmware that is executed in a standalone computer or in a processing system built into the measurement equipment, can process the data to determine a surface profile and the extent, severity, and location of subsurface damage. During the analysis, a factor or look-up table can be applied to correct for effects that the material of the optical element may have on the location of the focus point or the intensity of reflected light collected by the microscope. In particular, the vertical size of a measured defect may require compensation due to the different effect of the index of refraction. Based on actual measurements, each optical element produced in a manufacturing process can be identified as being operational or defective or can be graded according to the nature of the subsurface damage. Further, the evaluation can be conducted in a relatively short time, often as short as a few minutes, using equipment such as a laser microscope that is commercially available and relatively inexpensive.

Although the invention has been described with reference to particular embodiments, the description is only an example of the invention's application and should not be taken as a limitation. Various adaptations and combinations of features of the embodiments disclosed are within the scope of the invention as defined by the following claims.

What is claimed is:

1. A process for evaluating subsurface damage in an optical element, comprising:
   illuminating the optical element, with light characterized by a wavelength;
   focusing a measurement device at a measurement point that is within the optical element;
   measuring an intensity of scattered light at the wavelength that is scattered by a defect at the measurement point and collected by the measurement device when focusing at the measurement point;
   changing the measurement point; and
   repeating the measuring and changing steps to obtain intensity measurements for a set of points that are within the optical element.

2. The process of claim 1, further comprising analyzing the intensity measurements to determine locations of the subsurface damage in the optical element.

3. The process of claim 1, further comprising analyzing the intensity measurements to evaluate severity of the subsurface damage in the optical element.

4. The process of claim 1, wherein the subsurface damage being evaluated results from machining of the optical element.

5. The process of claim 4, wherein the machining includes one or more processes selected from a group consisting of grinding, diamond turning, and polishing.

6. The process of claim 1, wherein illuminating the optical element comprises focusing an optical beam at the same measurement point at which the measurement device is focused.

7. A process for evaluating subsurface damage in an optical element, comprising:
   illuminating the optical element;
   focusing a measurement device at a measurement point that is within the optical element;
   measuring an intensity of scattered light collected by the measurement device when focusing at the measurement point;
   changing the measurement point; and
   repeating the measuring and changing steps to obtain intensity measurements for a set of points that are within the optical element,
   wherein illuminating the optical element comprises illuminating the optical element with light having a wavelength corresponding to a dimension characteristic of subsurface defects.

8. A process for evaluating subsurface damage in an optical element, comprising:
   illuminating the optical element;
   focusing a measurement device at a measurement point that is within the optical element;
   measuring an intensity of scattered light collected by the measurement device when focusing at the measurement point;
   changing the measurement point; and
   repeating the measuring and changing steps to obtain intensity measurements for a set of points that are within the optical element,
   wherein the measurement device comprises a laser microscope that illuminates the optical element and collects light scattered within the optical element.

9. The process of claim 8, wherein the laser microscope comprises a laser emitting red light.

10. The process of claim 8, wherein the laser microscope comprises a laser emitting blue light.

11. A process for evaluating subsurface damage in an optical element, comprising:
    illuminating the optical element;
    focusing a measurement device at a measurement point that is within the optical element;
    measuring an intensity of scattered light collected by the measurement device when focusing at the measurement point;
    changing the measurement point; and
    repeating the measuring and changing steps to obtain intensity measurements for a set of points that are within the optical element,
    wherein repetitions of the step of changing the measurement point comprises moving the focus of the measurement device vertically to a series of points that are at different depths within the optical element.

12. The process of claim 11, wherein repetitions of the step of changing the measurement point further comprises moving the focus of the measurement device along a direction substantially parallel to a surface of the optical element.

* * * * *